United States Patent
VanDusseldorp

[11] Patent Number: 5,759,183
[45] Date of Patent: Jun. 2, 1998

[54] VAPORIZING ROLLER FOR AN ELECTROSURGICAL PROBE

[76] Inventor: Gregg A. VanDusseldorp, 2177-A Greenvalley Dr. Lake County, Crown Point, Ind. 46307

[21] Appl. No.: 865,313

[22] Filed: May 29, 1997

Related U.S. Application Data

[60] Provisional application No. 60/030,037 Nov. 5, 1996.
[51] Int. Cl.⁶ .................................................. A61B 17/36
[52] U.S. Cl. ........................... 606/46; 606/45; 606/49; 606/50
[58] Field of Search .................... 606/45, 46, 48, 606/49, 50, 41; 607/147

[56] References Cited

U.S. PATENT DOCUMENTS

| | | | |
|---|---|---|---|
| 1,103,669 | 7/1914 | Gibbs | 607/147 |
| 5,395,363 | 3/1995 | Billings et al. | 606/48 |
| 5,549,605 | 8/1996 | Hahnen | 606/46 |
| 5,599,349 | 2/1997 | D'Amelio | 606/46 |

*Primary Examiner*—Michael Powell Buiz
*Assistant Examiner*—Julian W. Woo
*Attorney, Agent, or Firm*—Gary M. Hartman; Domenica N. S. Hartman

[57] ABSTRACT

A roller (20) for an electrocautery probe or electrode (30), such as of the type used with a resectoscope. The roller (20) generally has a conductive body with an axis of rotation (26) and a surface with a circular cross-section in a plane perpendicular to the axis of rotation (26). The roller (20) further includes surface features (22) for generating circular-shaped areas of focused current concentration (24) in a radial direction relative to the axis of rotation (26) of the roller (20). For this purpose, recesses can be formed in the surface of the roller (20), with each recess defining a circular-shaped edge at the roller surface. Examples of suitable recesses include cylindrically-shaped perforations and concave impressions in the surface of the roller (20).

20 Claims, 2 Drawing Sheets

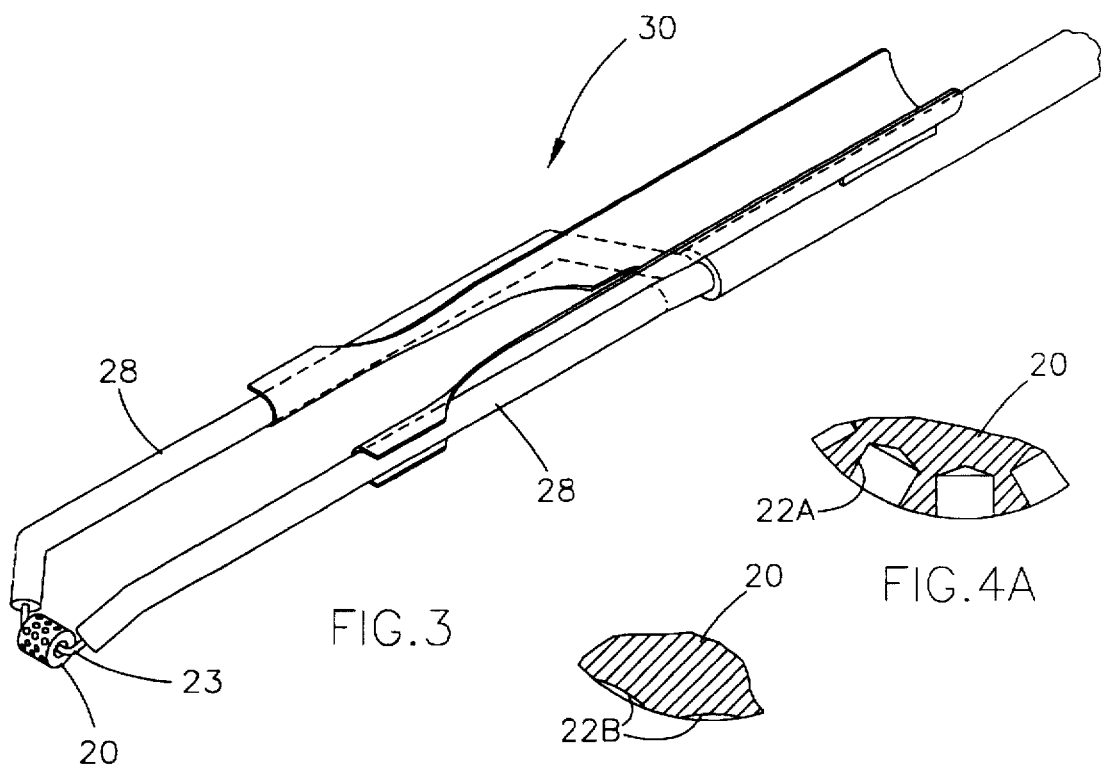
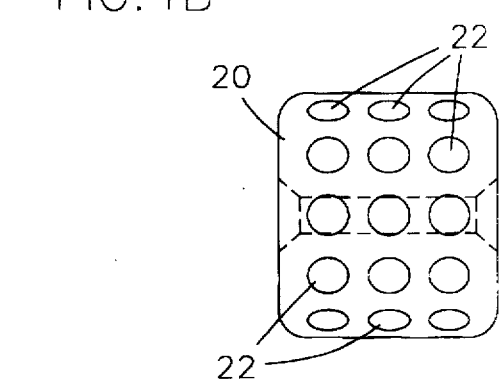

VAPORIZING ROLLER FOR AN ELECTROSURGICAL PROBE

CROSS REFERENCE TO RELATED APPLICATIONS

This application claims the benefit of U.S. Provisional Application Ser. No. 60/030,037, filed Nov. 5, 1996.

BACKGROUND OF THE INVENTION

1. Field of the Invention

The present invention generally relates to electrosurgical probes. More particularly, this invention relates to a vaporizing roller for an electrosurgical probe or electrode of the type used with a resectoscope, wherein the roller is characterized by a surface with multiple circular-shaped edges that promote complete coverage of the surgical area, create circular-shaped areas of focused high current concentration, and provide a high degree of vaporizing efficiency with improved coagulation at typical current settings.

2. Description of the Prior Art

Electrosurgical resection is a procedure in which damaged, diseased or enlarged tissue is removed with an electrocautery probe. An example is transurethral resection of the prostate (TURP), in which prostate tissue is removed by means of an electrocautery probe (e.g., a cutting loop) that is passed through the urethra by means of a resectoscope. This procedure has served as the historical treatment of benign prostate hypertrophy (BPH), cancer and prostatitus. Another example is endometrial ablation, which is an electrosurgical alternative treatment to hysterectomy in women with menorrhagia (abnormal uterine bleeding). In this case, an electrosurgical probe is passed through the vagina by means of a hysteroscope.

As understood by those skilled in the art, ablation and resection are electrosurgical effects accomplished by applying a highly damped radio frequency (RF) current to the tissue through an electrosurgical probe. Such current has been found to cut and/or coagulate tissue depending on the power and wave length combinations. The active tip of the electrosurgical probe is in direct view of the surgeon at all times through the telescope which is part of the resectoscope. Electrosurgical probes have been available for some time in a number of shapes and sizes. U.S. Pat. No. 4,917,082 to Grossi et al. illustrates a number of resectoscope electrode (probe) types such as coagulating electrodes, knife electrodes, punctate electrodes, and roller electrodes, etc.

More recently, roller or "roller bar" electrodes have been offered for use in endometrial ablation and prostatic resection. Such rollers are said to vaporize the tissue, leaving no chip or remnant tissue after application, while at the same time coagulating the tissue in the resected area to avoid operative and postoperative bleeding. A probe of this type is shown in FIG. 1. The probe is equipped with a roller 10 having a cylindrical shape and a number of circumferential grooves 12 in its cylindrical outer surface. The roller 10 is supported by two axle wires 13 that support the roller 10 and also provide electrical connection for the roller 10 to a suitable current source. Other known rollers, such as that disclosed in U.S. Pat. No. 5,549,605 to Hahnen, have one or more horizontal and/or circumferential grooves (the latter of which is referred to as "radial" grooves) intended to increase the surface area of the roller while maintaining the small overall size.

These more recent roller or "roller bar" probes are said to have grooves to increase the surface area of the roller. The presence of cutting grooves in the surface of the roller can provide for adequate vaporization, yet inadequate coagulation. In this case, medical professionals may elect to increase power from the electrosurgical generator to maintain acceptable performance, which undesirably increases the potential for electrical shock to both patient and surgeon. Additionally, the grooves concentrate current such that an uneven cut results, as is apparent from FIG. 1, requiring additional cuts and operating time to remove adequate amounts of tissue.

Thus, it would be desirable if an improved electrocautery probe (electrode) was available for performing electrosurgical resection procedures, wherein the probe promoted complete coverage of the surgical area while simultaneously providing a high degree of vaporizing efficiency with improved coagulation at safe and acceptable current settings.

SUMMARY OF THE INVENTION

It is an object of this invention to provide a roller for an electrosurgical probe, such as a resectoscope, characterized by the ability to create circular-shaped areas of focused high current concentration.

It is a further object of this invention that the areas of focused high current concentration are generated by surface features that define circular-shaped edges on the outer surface of the roller.

It is another object of this invention that the performance of the roller is characterized by balancing the relationship between the mass of the roller and the surface area of the roller, such that vaporization and coagulation occur simultaneously and to a desired degree.

In accordance with a preferred embodiment of this invention, these and other objects and advantages are accomplished as follows.

According to the present invention, there is provided a vaporizing roller for an electrocautery probe, such as a resectoscope. The roller generally has a conductive body with an axis of rotation and a surface with a circular cross-section in a plane perpendicular to the axis of rotation. The roller further includes means for generating circular-shaped areas of focused current concentration in a radial direction relative to the axis of rotation of the body. For this purpose, features can be formed in the surface of the body, with each feature defining a circular-shaped edge at the surface of the body.

Notably, the roller of this invention avoids the prior art use of grooves to increase the surface area of a roller for an electrocautery probe, and therefore avoids the reduced performance and uneven cut results associated with such rollers and their current concentration pattern, depicted in FIG. 1. According to this invention, the actual surface area of a roller has been determined to have little effect on the performance of the roller. Instead, this invention is based on the determination that a key to enhanced performance is balancing the relationship between the mass of a roller and its surface area, such that vaporization and coagulation occur simultaneously and to a desired degree.

Various roller configurations have been found to achieve this result, such as by forming recesses, such as cylindrically-shaped perforations or concave impressions, in the surface of the roller body. The recesses can be aligned in multiple circumferential rows, multiple axial rows, or combinations thereof. The recesses may be limited to the surface of the body, or may extend through the body. With surface recesses of this type, a balance between the mass and surface area of the roller has been achieved, with the result of increased coverage and focused current concentration that provide a high degree of vaporizing efficiency with improved coagulation at normal current settings. Consequently, the roller of this invention enables surgical procedure time to be reduced while simultaneously promoting safety for both the patient and the doctor performing the electrosurgical resection procedure.

Other objects and advantages of this invention will be better appreciated from the following detailed description.

BRIEF DESCRIPTION OF THE DRAWINGS

FIG. 3 is a perspective view of a resectoscope probe equipped with the roller of FIG. 2;

FIGS. 4A through 4C illustrate exemplary cross-sectional configurations for surface features formed in the cylindrical surface of the roller of FIG. 2; and FIGS. 5A through 5C illustrate alternative surface feature patterns for the roller of FIG. 2 in accordance with this invention.

DETAILED DESCRIPTION OF THE PREFERRED EMBODIMENT

Figure 1:
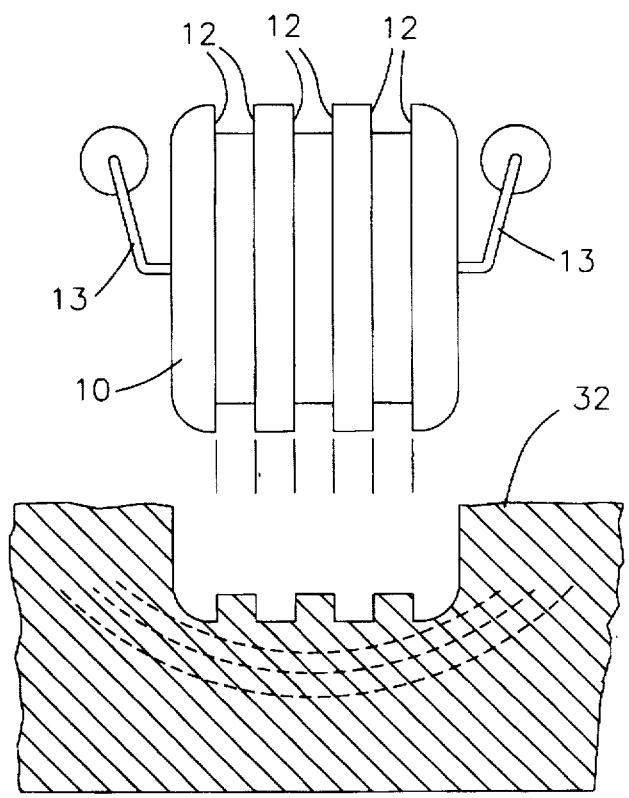
FIG. 1 is a front view of an electrocautery probe equipped with a roller in accordance with the prior art.
Figure 2:
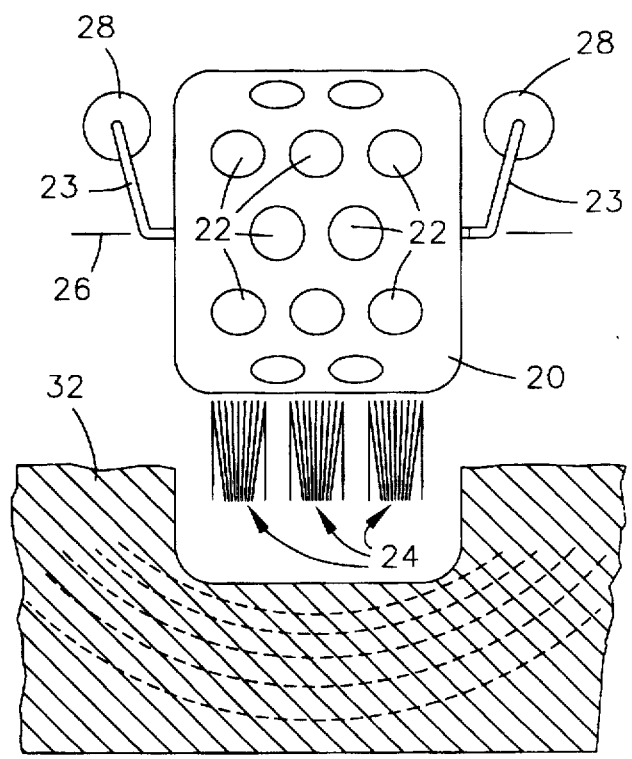
FIG. 2 is a front view of an electrocautery probe equipped with a roller in accordance with an embodiment of this invention.

A resectoscope vaporizing roller 20 in accordance with a first embodiment of this invention is shown in FIGS. 2 and 3, with alternative roller embodiments shown in FIGS. 4A through 4C and 5A through 5C. FIG. 3 shows the roller 20 mounted to an electrocautery probe (electrode) 30 of a known configuration. The probe 30 is generally configured to include a pair of electrically-conductive arms 28, between which an electrically-conductive axle wire 23 extends for rotatably mounting the roller 20 to the arms 28. The roller 20 is constructed of any suitable conductive material, with a preferred material being a nickel silver alloy, as is conventional in the art.

As shown in FIGS. 2 and 3, the roller 20 has a generally cylindrical shape, though the roller 20 could alternatively have a spherical or ellipsoid shape. Generally, the roller 20 can be described as having a circular-shaped cross-section in a plane perpendicular to an axis of rotation 26 of the roller 20, as is evident from the Figures. The cross-section of the roller 20 need not be uniform along the axis of rotation 26, but instead can include concave or convex surfaces that form surface regions parallel and/or perpendicular to the axis of rotation 26 of the roller 20.

In the embodiment of FIGS. 2 and 3, the roller 20 is shown as having surface features 22 that form circular-shaped edges on the outer cylindrical surface of the roller 20. Various surface features 22 are capable of forming the desired circular-shaped edges, such as cylindrically-shaped perforations 22A and concave impressions 22B shown in FIGS. 4A and 4B, respectively, which form edges that might more accurately be described as oval given the circular cross-section of the roller 20 shown in FIG. 2. According to the invention, the surface features 22 are of controlled depth and/or diameter to maintain a desirable mass/surface area relationship for the roller 20, which can be qualified experimentally. While shown as having axes of symmetry perpendicular to the axis or rotation 26 of the roller 20, the surface features 22 may be oriented at any angle relative to the surface and axis of rotation 26 of the roller 20. Furthermore, the surface features 22C may also penetrate the roller 20 completely, e.g., diametrically as shown in FIG. 4C, thus providing aeration and cooling during the application of current.

Importantly, the surface features 22 are arranged in patterns that provide more complete coverage of a surgical area, leaving a smooth postoperative application surface as illustrated in FIG. 2. A preferred pattern is shown in FIG. 2, with axial rows of features 22 equi-angularly spaced around the circumference of the roller 20, and in alternating numbers of two and three features 22. Alternate patterns are shown in FIGS. 5A, 5B and 5C. FIG. 5B shows the features 22 segregated in discrete axial rows. FIG. 5C shows the features 22 segregated in discrete circumferential rows, while FIG. 5A shows a full array of axial and circumferential rows of features 22 that uniformly cover the surface of the roller 20.

According to this invention, the circular-shaped edges created by the intersection of the surface features 22 and the cylindrical surface of the roller 20 has been determined to advantageously generate circular-shaped areas of focused high current concentration 24 at the surface of tissue 32 being treated, as represented in FIG. 2. Also according to this invention, the size, shape and depth of the surface features 22 can be tailored to provide specific areas of current concentration that may vary depending on tissue type or anatomic shape. The focused current concentration 24, in combination with the balanced mass/surface area relationship and increased surface coverage achieved by the surface features 22 of this invention, provide a high degree of vaporizing efficiency with improved coagulation at normal current settings. This reduces surgical procedure time and reduces safety concerns.

While the invention has been described in terms of a preferred embodiment, it is apparent that other forms could be adopted by one skilled in the art. For example, the shape, size and material for the roller of this invention, as well as an electrocautery probe or electrode equipped with the roller, could differ from that noted. Accordingly, the scope of the invention is to be limited only by the following claims.

What is claimed is:

1. A roller for an electrocautery probe, the roller comprising:
   a conductive body having an axis of rotation and a surface with a circular cross-section in a plane perpendicular to the axis of rotation; and
   means for generating circular-shaped areas of focused current concentration in a radial direction relative to the axis of rotation of the body.

2. A roller as recited in claim 1, wherein the generating means comprises recesses in the surface of the body, each recess forming a circular-shaped edge at the surface of the body.

3. A roller as recited in claim 2, wherein the recesses are cylindrically-shaped perforations in the surface of the body.

4. A roller as recited in claim 2, wherein the recesses are concave impressions in the surface of the body.

5. A roller as recited in claim 2, wherein the recesses are aligned in multiple circumferential rows.

6. A roller as recited in claim 2, wherein the recesses are aligned in multiple axial rows equi-angularly spaced around the surface of the body.

7. A roller as recited in claim 2, wherein the recesses are aligned in multiple axial and circumferential rows.

8. A roller as recited in claim 2, wherein the recesses extend through the body of the roller.

9. A roller as recited in claim 1, wherein the body has a cylindrically-shaped surface with an axis of symmetry coinciding with the axis of rotation of the body.

10. A roller as recited in claim 1, wherein the roller is attached to an electrocautery probe.

11. A roller as recited in claim 10, further comprising wires that rotatably secure the roller to the electrocautery probe.

12. An electrocautery probe comprising:

a pair of arms;

an electrically-conductive axle interconnecting the pair of arms;

a roller having a conductive body with an axis of rotation defined by the axle and a surface with a circular cross-section in a plane perpendicular to the axis of rotation; and means for generating circular-shaped areas of focused current concentration in a radial direction relative to the axis of rotation of the body.

13. An electrocautery probe as recited in claim 12, wherein the generating means comprises recesses formed in the surface of the roller, each recess forming a circular-shaped edge at the surface of the body.

14. An electrocautery probe as recited in claim 13, wherein the recesses are cylindrically-shaped perforations in the surface of the roller.

15. An electrocautery probe as recited in claim 13, wherein the recesses are concave impressions in the surface of the roller.

16. An electrocautery probe as recited in claim 13, wherein the recesses are aligned in multiple circumferential rows.

17. An electrocautery probe as recited in claim 13, wherein the recesses are aligned in multiple axial rows equi-angularly spaced around the surface of the body.

18. An electrocautery probe as recited in claim 13, wherein the recesses are aligned in multiple axial and circumferential rows.

19. An electrocautery probe as recited in claim 13, wherein the recesses extend diametrically through the body of the roller.

20. An electrocautery probe as recited in claim 12, wherein the surface of the roller is cylindrically-shaped and has an axis of symmetry coinciding with the axis of rotation of the body.

* * * * *